US008357354B2

(12) United States Patent
Ilekti et al.

(10) Patent No.: US 8,357,354 B2
(45) Date of Patent: Jan. 22, 2013

(54) COMPOSITION CONTAINING A TACKIFYING RESIN AND A COMBINATION OF PARTICULAR OILS

(75) Inventors: Philippe Ilekti, Maison-Alfort (FR); Sylvie Guillard, Chevry Cossigny (FR)

(73) Assignee: L'Oreal, Paris (FR)

( * ) Notice: Subject to any disclaimer, the term of this patent is extended or adjusted under 35 U.S.C. 154(b) by 189 days.

(21) Appl. No.: 12/817,465

(22) Filed: Jun. 17, 2010

(65) Prior Publication Data

US 2011/0002864 A1     Jan. 6, 2011

Related U.S. Application Data

(60) Provisional application No. 61/222,126, filed on Jul. 1, 2009.

(30) Foreign Application Priority Data

Jun. 19, 2009    (FR) ...................................... 09 54173

(51) Int. Cl.
*A61K 8/81*     (2006.01)
*A61Q 1/04*     (2006.01)

(52) U.S. Cl. ..................... 424/64; 424/70.11; 424/70.12

(58) Field of Classification Search ........................ None
See application file for complete search history.

(56) References Cited

U.S. PATENT DOCUMENTS

| 4,873,078 A | 10/1989 | Edmundson et al. |
| 2005/0201961 A1* | 9/2005 | Lu et al. ........................... 424/63 |
| 2006/0008485 A1* | 1/2006 | Ferone et al. ................. 424/401 |
| 2006/0134035 A1 | 6/2006 | Zheng et al. |
| 2007/0014745 A1 | 1/2007 | Arnaud et al. |
| 2007/0258934 A1 | 11/2007 | Bui et al. |
| 2008/0102049 A1* | 5/2008 | McDermott .................... 424/64 |

FOREIGN PATENT DOCUMENTS

| EP | 1 044 674 | 10/2000 |
| EP | 1 604 632 | 12/2005 |
| EP | 1 661 549 | 5/2006 |
| EP | 1 743 627 | 1/2007 |
| EP | 1 854 451 | 11/2007 |
| EP | 1 944 915 | 7/2008 |
| FR | 933963 | 5/1948 |
| FR | 2 904 218 | 2/2008 |
| FR | 2 918 272 | 1/2009 |

* cited by examiner

*Primary Examiner* — Robert A Wax
*Assistant Examiner* — Randeep Singh
(74) *Attorney, Agent, or Firm* — Oblon, Spivak, McClelland, Maier & Neustadt, L.L.P.

(57) ABSTRACT

A composition having at least one fatty phase containing at least one resin having a number-average molecular weight of less than or equal to 10 000 g/mol chosen from rosin, rosin derivatives and hydrocarbon-based resins, and mixtures thereof, at least one volatile oil, and at least one phenyl silicone oil. The composition according to the invention makes it possible to obtain a homogeneous and comfortable deposit on the lips or the skin, which has in particular improved properties of staying power of the colour and of the gloss.

19 Claims, No Drawings

COMPOSITION CONTAINING A TACKIFYING RESIN AND A COMBINATION OF PARTICULAR OILS

REFERENCE TO PRIOR APPLICATIONS

This application claims priority to U.S. provisional application Ser. No. 61/222,126, filed Jul. 1, 2009; and to French patent application 09 54173, filed Jun. 19, 2009, both incorporated herein by reference.

FIELD OF THE INVENTION

The present invention relates to a composition containing a tackifying resin and a combination of particular oils. In preferred embodiments cosmetic makeup and/or care compositions, in particular for the skin and the lips, are described.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

BACKGROUND OF THE INVENTION

In the cosmetics field, the development of formulations having both good properties in terms of application and comfort and satisfactory properties in terms of staying power, in particular staying power of the gloss and migration resistance, is a continual objective.

Document EP 1 405 625 discloses lipstick compositions based on phenyl silicone oil for obtaining a glossy makeup on the lips. However, 2 hours after application to the lips, the glossy appearance lessens, thus resulting in a less effective makeup result.

Consequently, there remains at this time a need for a makeup and/or care composition for the lips or the skin, which is homogeneous and has improved staying power of the gloss, and which forms a homogeneous deposit after application to the skin or the lips.

DETAILED DESCRIPTION OF THE PREFERRED EMBODIMENTS

Unexpectedly, the inventors have noted that the combination of phenyl silicone oil with a particular tackifying resin and a volatile oil makes it possible to obtain a homogeneous composition which provides a deposit on, e.g., the skin or the lips that is glossy on application and that remains glossy after 2 hours.

Moreover, the compositions according to the invention are also very satisfactory in terms of ease of application (glidance and disintegration) and of comfort.

In a preferred embodiment, the present invention relates to a composition, preferable a cosmetic makeup and/or care composition, comprising at least one fatty phase comprising:
  at least one resin (also called "tackifying resin") having a number-average molecular weight of less than or equal to 10 000 g/mol, chosen from rosin, rosin derivatives and hydrocarbon-based resins, and mixtures thereof,
  at least one volatile oil, and
  at least one phenyl silicone oil.

According to another aspect, a subject of the invention is also a cosmetic method for making up keratin materials, and in particular the lips, comprising the application to said keratin materials, and in particular the lips, of a composition as defined above.

Another subject of the invention is the use of a composition as described above for making up the skin or the lips so as to obtain a deposit on the skin or the lips which has satisfactory properties in terms of homogeneity of the deposit and/or of gloss and/or of staying power of the gloss and/or of staying power of the colour.

Tackifying Resin

The resin (also called tackifying resin) used in the composition according to the invention has a number-average molecular weight of less than or equal to 10 000 g/mol, in particular ranging from 250 to 10 000 g/mol, preferably less than or equal to 5000 g/mol, in particular ranging from 250 to 5000 g/mol, better still less than or equal to 2000 g/mol, in particular ranging from 250 to 2000 g/mol, and even better still less than or equal to 1000 g/mol, in particular ranging from 250 to 1000 g/mol.

The number-average molecular weights (Mn) are determined by gel permeation liquid chromatography (THF solvent, calibration curve established with linear polystyrene standards, refractometric detector).

The resin of the composition according to the invention is advantageously a tackifying resin. Such resins are described especially in the Handbook of Pressure Sensitive Adhesive, edited by Donatas Satas, 3rd edition, 1989, pp. 609-619, incorporated herein by reference.

The resin of the composition according to the invention is preferably chosen from rosin, rosin derivatives and hydrocarbon-based resins, and mixtures thereof, and especially preferably from hydrocarbon-based resins.

Rosin is a mixture predominantly comprising organic acids known as rosin acids (mainly acids of abietic type and of pimaric type).

Three types of rosin exist: rosin ("gum rosin") obtained by incision on live trees, wood rosin, which is extracted from pine wood or stumps, and tall oil ("tall oil rosin"), which is obtained from a by-product originating from the production of paper.

The rosin derivatives may be derived in particular from the polymerization, hydrogenation and/or esterification (for example with polyhydric alcohols such as ethylene glycol, glycerol or pentaerythritol) of rosin acids. Examples that may be mentioned include the rosin esters sold under the reference Foral 85, Pentalyn H and Staybelite Ester 10 by the company Hercules; Sylvatac 95 and Zonester 85 by the company Arizona Chemical, or Unirez 3013 by the company Union Camp.

The hydrocarbon-based resins are preferably chosen from low molecular weight polymers that may be classified, according to the type of monomer they comprise, as:
  indene hydrocarbon-based resins such as the resins resulting from the polymerization in major proportion of an indene monomer and in minor proportion of a monomer chosen from styrene, methylindene and methylstyrene, and mixtures thereof, these resins possibly being hydrogenated. These resins may have a molecular weight ranging from 290 to 1150 g/mol.
  Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp., or the hydrogenated indene/methyl-styrene/styrene copolymers such as those sold under the name "Regalite" by the company Eastman Chemical, in particular Regalite R1100, Regalite R1090, Regalite R7100, Regalite R1010 Hydrocarbon Resin and Regalite R1125 Hydrocarbon Resin;

aliphatic pentanediene resins such as those derived from the majority polymerization of the 1,3-pentanediene (trans or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500 g/mol.

Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentadiene dimers such as those derived from the polymerization of first monomers chosen from indene and styrene, and of second monomers chosen from cyclopentadiene dimers such as dicyclopentadiene, methyldicyclopentadiene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, β-pinene and limonene, and mixtures thereof. These resins may have a molecular weight ranging from 300 to 2000 g/mol. Such resins are sold, for example, under the names Piccolyte A115 and S125 by the company Hercules, and Zonarez 7100 or Zonatac 105 Lite by the company Arizona Chem;

hydrogenated C6-C20 polyolefins such as those sold under the names Eastotac H-142W, Eastotac H-142R and Eastotac H-100W by the company Eastman Chemical Co.

According to one preferred embodiment, the resin is chosen from indene hydrocarbon-based resins, which are preferably hydrogenated. The indene hydrocarbon-based resin preferably results from the polymerization of an indene monomer and of a monomer chosen from styrene, methylindene and methylstyrene, and mixtures thereof. As hydrogenated indene hydrocarbon-based resin, mention may in particular be made of hydrogenated indene/methylstyrene/styrene copolymers such as those sold under the name "Regalite" by the company Eastman Chemical, for instance Regalite R 1100, Regalite R 1090, Regalite R-7100, Regalite R1010 Hydrocarbon Resin and Regalite R1125 Hydrocarbon Resin.

The tackifying resin may be present in the composition according to the invention in a content ranging from 0.1% to 30% by weight, relative to the total weight of the composition, preferably ranging from 0.3% to 20% by weight, more preferably ranging from 0.5% to 15% by weight.

Liquid Fatty Phase

The fatty phase of the composition according to the invention may comprise at least one oil.

The term "oil" is intended to mean a nonageuous, water-immiscible compound which is liquid at ambient temperature (25° C.) and atmospheric pressure (760 mmHg).

Phenyl Silicone Oil

The composition according to the invention comprises at least one phenyl silicone oil. The term "phenyl silicone oil" (or "phenyl silicone") is intended to mean an organopolysiloxane comprising at least one phenyl group.

The phenyl silicone oil is preferably non-volatile.

The term "non-volatile oil" is intended to mean an oil that remains on the skin or the keratin fibre, more generally on the keratin material, at ambient temperature and atmospheric pressure, at least for several hours and that has in particular a vapour pressure of less than $10^{-3}$ mmHg (0.13 Pa). A non-volatile oil can also be defined as having a rate of evaporation such that, under the conditions previously defined, the amount evaporated after 30 minutes is less than 0.07 mg/cm².

Preferably, the molecular weight of the phenyl silicone oil is between 500 and 100 000 g/mol.

Preferably, the phenyl silicone oil is chosen from the group constituted of the compounds of formulae (I), (II), (III), (IV) and (V) below:

Compounds of formula (I)

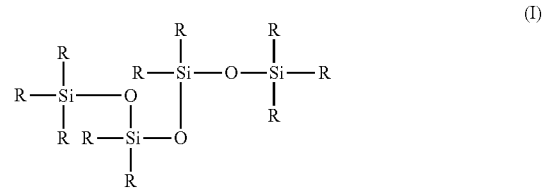

Compounds of formula (II)

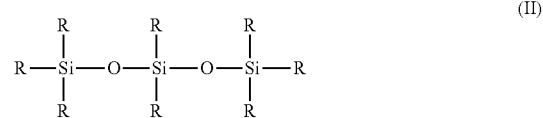

formulae (I) and (II) being such that the R groups independently represent a methyl group or a phenyl group, and that at least three of the R radicals are phenyl groups, or even at least four, in particular at least five. Use may, for example, be made of trimethyl-pentaphenyltrisiloxane (or 1,3,5-trimethyl-1,1,3,5,5-pentaphenyltrisiloxane) sold under the reference PH-1555 HR1 by the company Dow Corning;

Compounds of formula (III)

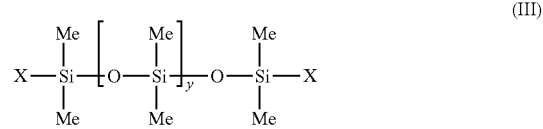

in which X represents a —CH$_2$—CH(CH$_3$) (Ph) group, Me represents a methyl group and Ph a phenyl group, and y varies between 1 and 10 000, Compounds of formula (IV)

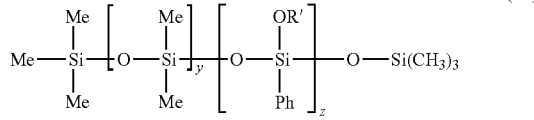

in which Me is methyl and Ph is phenyl, OR' represents an —OSiMe$_3$ group and y varies between 1 and 1000, z varies between 1 and 1000, such that the compound (IV) is a non-volatile oil. Use may, for example, be made of trimethyl siloxyphenyl dimethicone, in particular sold under the reference Belsil PDM 1000 marketed by the company Wacker;

Compounds of Formula (V)

in which R represents a phenylpropyl group, and x and y vary, independently of one another, between 1 and 10 000, such that x+y is sufficiently high for the compound (V) to be a non-volatile oil. Use may, for example, be made of the phenylpropyldimethylsiloxy-silicate sold under the reference SilShine 151 marketed by GE Silicones.

According to one particular embodiment, the composition according to the invention contains at least one phenyl silicone oil of formula (IV), as defined above.

The phenyl silicone oil of formula (II), (III), (IV) or (V), preferably has a refractive index of greater than 1.4, in particular less than 1.6.

The phenyl silicone oils have a viscosity advantageously chosen in the range of from 5 to 800 000 mm$^2$/s at 25° C., preferably from 10 to 500 000 mm$^2$/s, and better still from 10 to 5000 mm$^2$/s.

Preferably, the phenyl silicone oil is present in the composition according to the invention in a content ranging from 0.5% to 85% by weight, particularly from 5% to 70% by weight, and for example from 10% to 60% by weight, relative to the total weight of the composition.

Advantageously, the composition comprises between 10% and 85% by weight of phenyl silicone oil, relative to the total weight of the composition, preferably between 15% and 70%, between 15% and 60%, and more preferably between 15% and 40%.

Preferably, the weight ratio of phenyl silicone oil to tackifying resin ranges from 1 to 5, and more preferably from 1.5 to 4, preferably from 2 to 3.5, or even better still from 2.5 to 3.5.

Volatile Oil

The composition according to the invention comprises at least one volatile oil.

For the purpose of the invention, a volatile oil has, at ambient temperature (25° C.) and atmospheric pressure (760 mmHg) a vapour pressure ranging from 0.02 mmHg to 300 mmHg (2.66 Pa to 40 000 Pa) and better still ranging from 0.1 to 90 mmHg (13 Pa to 12 000 Pa). The non-volatile oils then correspond to a vapour pressure of less than 0.02 mmHg (2.66 Pa), and better still less than 10$^{-3}$ mmHg (0.13 Pa).

The volatile oil may be a silicone oil, a hydrocarbon-based oil or a fluoro oil.

a. Silicone Oil

According to one variant of the invention, the liquid fatty phase comprises at least one volatile silicone oil.

The term "silicone oil" is intended to mean an oil comprising at least one silicon atom, and in particular comprising Si—O groups.

The volatile silicone oil that can be used in the invention may be chosen from silicone oils having a flash point ranging from 40° C. to 150° C., preferably having a flash point of greater than 55° C. and less than or equal to 105° C., and preferentially ranging from 65° C. to 95° C. The flash point is in particular measured according to ISO standard 3679.

The volatile silicone oil may be chosen from linear or cyclic silicone oils such as linear or cyclic polydimethylsiloxanes (PDMSs) having from 3 to 7 silicon atoms.

By way of example of such oils, mention may be made of octyl trimethicone, hexyl trimethicone, decamethylcyclopentasiloxane (cyclopentasiloxane or D5), octamethylcyclotetrasiloxane (cyclotetradimethyl-siloxane or D4), dodecamethylcyclohexasiloxane (D6), decamethyltetrasiloxane (L4), KF 96 A from Shin Etsu, and polydimethylsiloxanes such as those sold under the reference DC 200 (1.5 cSt), DC 200 (5 cSt) and DC 200 (3 cSt) by Dow Corning.

b. Hydrocarbon-Based Oil

According to one variant of the invention, the liquid fatty phase comprises at least one volatile hydrocarbon-based oil.

The term "hydrocarbon-based oil" is intended to mean an oil formed essentially, or even constituted, of carbon and hydrogen atoms, and optionally of oxygen and nitrogen atoms, and containing no silicon or fluorine atoms. It may contain alcohol, ester, ether, carboxylic acid, amine and/or amide groups.

The volatile hydrocarbon-based oils (also called solvents) may be chosen from hydrocarbon-based oils containing from 8 to 16 carbon atoms, and in particular branched C8-C16 alkanes such as C8-C16 isoalkanes of petroleum origin (also called isoparaffins), for instance isododecane (also called 2,2,4,4,6-penta-methylheptane), isodecane or isohexadecane, and, for example, the oils sold under the trade names Isopars or Permethyls, branched C8-C16 esters, isohexyl neopentanoate, and mixtures thereof. Other volatile hydrocarbon-based oils, such as petroleum distillates, in particular those sold under the name Shell Solt by the company Shell, may also be used. Preferably, the volatile solvent is chosen from volatile hydrocarbon-based oils containing from 8 to 16 carbon atoms and mixtures thereof.

As other volatile hydrocarbon-based solvents (oils) that can be used in the composition according to the invention, mention may also be made of ketones which are liquid at ambient temperature, such as methyl ethyl ketone or acetone; short-chain esters (containing from 3 to 8 carbon atoms in total), such as ethyl acetate, methyl acetate, propyl acetate or n-butyl acetate; ethers which are liquid at ambient temperature, such as diethyl ether, dimethyl ether or dichlorodiethyl ether; alcohols, and in particular linear or branched lower monoalcohols containing from 2 to 5 carbon atoms, for instance ethanol, isopropanol or n-propanol.

Preferably, the composition has a volatile oil content of greater than 5% by weight, preferably ranging from 5% to 50% by weight, and ranging from 10% to 35% by weight, relative to the total weight of the composition.

According to one preferred embodiment, the volatile oil has a flash point of greater than 65° C., and better still greater than 80° C. By way of example of such a volatile oil, mention may be made of isohexadecane.

Non-Volatile Oils

The composition according to the invention may comprise, in addition to the volatile oil and the phenyl silicone oil, at least one other additional oil which is non-volatile. Said oil may in particular be chosen from non-volatile hydrocarbon-based and/or silicone and/or fluoro oils, and preferably from hydrocarbon-based oils.

The term "non-volatile oil" is intended to mean an oil which remains on the skin or the keratin fibre, more generally on the keratin material, at ambient temperature and atmospheric pressure, for at least several hours and which has in particular a vapour pressure of less than $10^{-3}$ mmHg (0.13 Pa). A non-volatile oil can also be defined as having a rate of evaporation such that, under the conditions defined above, the amount evaporated after 30 minutes is less than 0.07 mg/cm$^2$.

These oils may be of plant, mineral or synthetic origin.

As non-volatile hydrocarbon-based oil, mention may be made of:

hydrocarbon-based oils of plant origin, such as triglycerides constituted of fatty acid esters of glycerol, the fatty acids of which can have chain lengths ranging from $C_4$ to $C_{24}$, it being possible for these oils to be linear or branched, and saturated or unsaturated; for instance heptanoic or octanoic acid triglycerides; these oils are in particular wheatgerm oil, sunflower oil, grapeseed oil, sesame oil, maize oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, blackcurrant oil, evening primrose oil, millet oil, barley oil, quinoa oil, rye oil, safflower oil, candlenut oil, passion flower oil or musk rose oil; or caprylic/capric acid triglycerides, for instance those sold by the company Stéarineries Dubois or those sold under the names Miglyol 810®, 812® and 818® by the company Dynamit Nobel, synthetic ethers;

linear or branched hydrocarbons of mineral or synthetic origin, such as liquid paraffin or derivatives thereof, petroleum jelly, hydrogenated polyisobutene such as Parleam® sold by the company Nippon Oil Fats, squalane, polybutylenes such as Indopol H-100 (of molar mass or MW=965 g/mol), Indopol H-300 (MW=1340 g/mol), Indopol H-1500 (MW=2160 g/mol), sold or manufactured by the company Amoco, hydrogenated polyisobutylenes such as Panalane H-300 E sold or manufactured by the company Amoco (MW=1340 g/mol), Viseal 20000 sold or manufactured by the company Synteal (MW=6000 g/mol), Rewopal PIB 1000 sold or manufactured by the company Witco (MW=1000 g/mol), polydecenes and hydrogenated polydecenes, such as: Puresyn 10 (MW=723 g/mol) or Puresyn 150 (MW=9200 g/mol) sold or manufactured by the company Mobil Chemicals, and mixtures thereof;

fatty acid esters, in particular of 4 to 22 carbon atoms, and especially of octanoic acid, of heptanoic acid, of lanolic acid, of oleic acid, of lauric acid, or of stearic acid, for instance propylene glycol dioctanoate, propylene glycol monoisostearate, polyglyceryl-2 diisostearate or neopentyl glycol diheptanoate;

synthetic esters, for instance oils of formula $R_1COOR_2$ in which $R_1$ represents a linear or branched fatty acid residue containing from 1 to 40 carbon atoms and $R_2$ represents a hydrocarbon-based chain that is in particular branched, containing from 1 to 40 carbon atoms, on condition that $R_1+R_2 \geq 11$, for instance purcellin oil (cetostearyl octanoate), isononyl isononanoate, $C_{12}$ to $C_{15}$ alkyl benzoate, 2-ethylhexyl palmitate, 2-octyldodecyl stearate, 2-octyldodecyl erucate, isostearyl isostearate, 2-octyldodecyl benzoate, octanoates, decanoates or ricinoleates of alcohols or of polyalcohols, isopropyl myristate, isopropyl palmitate, butyl stearate, hexyl laurate, 2-ethylhexyl palmitate, 2-hexyldecyl laurate, 2-octyldecyl palmitate, 2-octydodecyl myristate or isodecyl neopentanoate;

hydroxylated esters, for instance isostearyl lactate, octyl hydroxystearate, octyldodecyl hydroxystearate, diisostearyl malate, triisocetyl citrate, and glyceryl or diglyceryl triisostearate; diethylene glycol diisononanoate;

pentaerythritol esters, for instance pentaerythrityl tetradecyl-2-tetradecanoate (MW=1538 g/mol), pentaerythrityl tetraisostearate (MW=1202 g/mol) or pentaerythrityl tetraisononanoate (MW=697 g/mol);

esters of aromatic acids and of alcohols containing 4 to 22 carbon atoms, in particular tridecyl trimellitate;

a polyester resulting from the esterification of at least one triglyceride of hydroxylated carboxylic acid(s) with an aliphatic monocarboxylic acid and with an aliphatic dicarboxylic acid, which is optionally unsaturated, such as the succinic acid and isostearic acid castor oil sold under the reference Zenigloss by Zenitech;

esters of dimer diol and of dimer diacid of general formula HO—$R^1$—(—OCO—$R^2$—COO—$R^1$)$_h$—OH, in which:

$R^1$ represents a dimer diol residue, which dimer diol is obtained by hydrogenation of dilinoleic diacid, $R^2$ represents a hydrogenated dilinoleic diacid residue, and h represents an integer varying from 1 to 9, in particular, the esters of dilinoleic diacids and of dilinoleic dimer diols sold by the company Nippon Fine Chemical under the trade name Lusplan DD-DA5® and DD-DA7®;

vinylpyrrolidone/1-hexadecene copolymers, for example sold under the name Antaron V-216 by the company ISP (MW=7300 g/mol);

fatty alcohols which are liquid at ambient temperature and which have a branched and/or unsaturated carbon chain containing from 8 to 26 carbon atoms, for instance oelyl alcohol, linolyl alcohol, linolyl alcohol, isostearyl alcohol or octyldodecanol; $C_8$-$C_{26}$ higher fatty acids such as oleic acid, linoleic acid, linolenic acid, or isostearic acid; and mixtures thereof.

The non-volatile silicone oils that can be used in the composition according to the invention, and that are different from the phenyl silicone oil, may be non-volatile polydimethylsiloxanes (PDMSs), polydimethyl-siloxanes comprising alkyl or alkoxy groups, which are pendent and/or at the end of the silicone chain, said groups each containing from 2 to 24 carbon atoms.

Preferably, the composition contains at least one non-volatile hydrocarbon-based oil chosen from vinyl-pyrrolidone/1-hexadecene copolymers, Antaron V-216 (also called Ganex V216) sold or manufactured by the company ISP (MW=7300 g/mol).

Preferably, the additional non-volatile oil (different from the phenyl silicone oil) may be present in a content ranging from 0.1% to 60% by weight, especially ranging from 0.5% to 50% by weight, and in particular ranging from 1% to 40% by weight, relative to the total weight of the composition.

In addition to the oils described above, the fatty phase may also comprise at least one fatty substance which is not liquid at ambient temperature (25° C.) and atmospheric pressure, called a solid fatty substance, chosen from waxes and pasty fatty substances.

Wax(es)

The wax under consideration in the context of the present invention is generally a lipophilic compound which is solid at ambient temperature (25° C.), which exhibits a reversible solid/liquid change of state and which has a melting point of greater than or equal to 30° C. which can range up to 200° C. and in particular up to 120° C.

In particular, the waxes suitable for the invention can exhibit a melting point of greater than or equal to 45° C., and in particular greater than or equal to 55° C.

For the purpose of the invention, the melting point corresponds to the temperature of the most endothermic peak observed by thermal analysis (DSC) as described in ISO standard 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

The waxes that may be used in the compositions according to the invention are chosen from waxes that are solid at room temperature of animal, plant, mineral or synthetic origin, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these waxes that may especially be mentioned are isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylol-propane) tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

A wax that may be used is a $C_{20}$-$C_{40}$ alkyl (hydroxystearyloxy)stearate (the alkyl group containing from 20 to 40 carbon atoms), alone or as a mixture.

Such a wax is especially sold under the names Kester Wax K 82 P®, Hydroxypolyester K 82 P® and Kester Wax K 80 P® by the company Koster Keunen.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 114S® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

According to one preferred embodiment of the invention, the composition comprises at least one wax.

Advantageously, the wax is chosen from hydrocarbon-based waxes, preferably from polyethylene waxes.

The composition according to the invention may comprise a content of waxes ranging from 0.1% to 30% by weight, relative to the total weight of the composition; it may in particular contain from 0.5% to 20%, more particularly from 1% to 15% thereof.

According to another embodiment, the composition according to the invention is free of wax. According to this embodiment, the composition is therefore preferably in liquid form.

According to one preferred embodiment, the composition according to the invention comprises at least one hydrocarbon-based resin (preferably chosen from hydrogenated indene/methylstyrene/styrene copolymers such as those sold under the name Regalite by the company Eastman Chemical, a non-volatile phenyl silicone oil, a volatile oil, an additional non-volatile oil, preferably chosen from vinylpyrrolidone/1-hexadecene copolymers and a polyethylene wax.

Pasty Compounds

The composition according to the invention may also comprise, in addition to the waxes, another solid fatty substance such as at least one pasty compound.

For the purpose of the present invention, the term "pasty" is intended to mean a lipophilic fatty compound which has a reversible solid/liquid change of state, which has an anisotropic crystalline organization in the solid state, and which comprises, at the temperature of 23° C., a liquid fraction and a solid fraction.

In other words, the starting melting point of the pasty compound may be less than 23° C. The liquid fraction of the pasty compound, measured at 23° C., can represent 9% to 97% by weight of the compound. This liquid fraction at 23° C. preferably represents between 15% and 85%, more preferably between 40% and 85% by weight.

The liquid fraction, by weight, of the pasty compound at 23° C. is equal to the ratio of the heat of fusion consumed at 23° C. to the heat of fusion of the pasty compound.

The heat of fusion of the pasty compound is the heat consumed by the compound in order to change from the solid state to the liquid state. The pasty compound is said to be in the solid state when all of its mass is in solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5 or 10° C. per minute, according to ISO standard 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample in order to change from the solid state to the state that it has at 23° C., made up of a liquid fraction and a solid fraction.

The liquid fraction of the pasty compound, measured at 32° C., preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same manner as the heat of fusion consumed at 23° C.

The pasty compound is preferably chosen from synthetic compounds and compounds of plant origin. A pasty compound may be obtained by synthesis from starting materials of plant origin.

The pasty compound may advantageously be chosen from:
lanolin and its derivatives
polymeric or non-polymeric silicone compounds
polymeric or non-polymeric fluoro compounds
vinyl polymers, in particular:
  olefin homopolymers and copolymers,
  hydrogenated diene homopolymers and copolymers,
  linear or branched oligomers, homopolymers or copolymers of alkyl (meth)acrylates preferably containing a $C_8$-$C_{30}$ alkyl group,
  oligomers, homopolymers and copolymers of vinyl esters containing $C_8$-$C_{30}$ alkyl groups,
  oligomers, homopolymers and copolymers of vinyl ethers containing $C_8$-$C_{30}$ alkyl groups,
liposoluble polyethers resulting from the polyetherification between one or more $C_2$-$C_{100}$ and preferably $C_2$-$C_{50}$ diols,
esters,
and mixtures thereof.
Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol,
the arachidyl propionate sold under the brand name Waxenol 801 by Alzo,
phytosterol esters,
fatty acid triglycerides and derivatives thereof,
pentaerythritol esters,
non-crosslinked polyesters resulting from the polycondensation between a linear or branched $C_4$-$C_{50}$ dicarboxylic acid or polycarboxylic acid and a $C_2$-$C_{50}$ diol or polyol,
aliphatic esters of an ester, resulting from the esterification of an aliphatic hydroxycarboxylic acid ester with an aliphatic carboxylic acid,
polyesters resulting from the esterification, with a polycarboxylic acid, of an aliphatic hydroxycarboxylic acid ester, said ester comprising at least two hydroxyl groups, such as the products Risocast DA-H® and Risocast DA-L®,
esters of dimer diol and dimer diacid, where appropriate esterified on their free alcohol or acid function(s) with acid or alcohol radicals, such as Plandool-G,
and mixtures thereof.

Among the pasty compounds of plant origin, a mixture of oxyethylenated (5OE) oxypropylenated (5OP) pentaerythritol and soy sterols, sold under the reference Lanolide by the company Vevy, will preferably be chosen.

According to a first embodiment, the composition comprises a total content of pasty fatty substance ranging from 0.5% to 50% by weight, relative to the total weight of the composition, preferably from 1% to 40%, or even better still from 5% to 30%.

According to another embodiment, the composition comprises less than 10% by weight, preferably less than 7%, better still less than 5%, and even better still less than 3% by weight of pasty fatty substance, relative to the total weight of the composition. More preferably, the composition is totally free of pasty fatty substance.

Filler

Advantageously, the composition according to the invention comprises at least one filler, in particular in a total content ranging from 0.01% to 50% by weight, relative to the total weight of the composition, preferably ranging from 0.01% to 30% by weight.

For the purpose of the present invention, the term "fillers" should be understood to mean white or colourless, mineral or synthetic particles of any form, which are insoluble in the medium of the composition irrespective of the temperature at which the composition is manufactured. These fillers serve in particular to modify the rheology or the texture of the composition.

The fillers may be mineral or organic of any form, platelet-shaped, spherical or oblong, irrespective of the crystallographic form (for example, lamellar, cubic, hexagonal, orthorhombic, etc.). Mention may be made of talc, mica, silica, kaolin, polyamide (Nylon®) powder (Orgasol® from Atochem), poly-β-alanine powder and polyethylene powder, powders of tetrafluoroethylene polymers (Teflon®), lauroyllysine, starch, boron nitride, hollow polymeric microspheres such as those of polyvinylidene chloride/acrylonitrile, for instance Expancel® (Nobel Industrie), or of acrylic acid copolymers (Polytrap® from the company Dow Corning) and silicone resin microbeads (Tospearls® from Toshiba, for example), polyurethane powders (for example Plastic Powder D-400® or Plastic Powder D-800® from the company Toshiki), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms, preferably from 12 to 18 carbon atoms, for example zinc stearate, magnesium stearate or lithium stearate, zinc laurate or magnesium myristate.

Structuring Agent/Thickener

The composition according to the invention may comprise, in addition to the waxes optionally present, at least one structuring agent chosen from lipophilic gelling agents and mixtures thereof.

Lipophilic Gelling Agents

According to one embodiment, the composition according to the invention may comprise at least one gelling agent. The gelling agents that can be used in the compositions according to the invention may be organic or mineral, polymeric or molecular lipophilic gelling agents.

Mineral lipophilic gelling agents that may be mentioned include optionally modified clays, for instance hectorites modified with a $C_{10}$ to $C_{22}$ ammonium chloride, for instance hectorite modified with distearyldimethylammonium chloride, such as, for example, the product sold under the name Bentone 38V® by the company Elementis.

Mention may also be made of fumed silica optionally subjected to a hydrophobic surface treatment, the particle size of which is less than 1 µm. It is in fact possible to chemically modify the surface of the silica, by chemical reaction generating a reduced number of silanol groups present at the surface of the silica. It is in particular possible to substitute silanol groups with hydrophobic groups: a hydrophobic silica is then obtained. The hydrophobic groups may be:
- trimethylsiloxyl groups, which are in particular obtained by treating fumed silica in the presence of hexamethyldisilazane. Silicas thus treated are known as silica silylate according to the CTFA (8th edition, 2000). They are sold, for example, under the references Aerosil R812® by the company Degussa, and Cab-O-Sil TS-530® by the company Cabot,
- dimethylsilyloxyl or polydimethylsiloxane groups, which are in particular obtained by treating fumed silica in the presence of polydimethylsiloxane or dimethyldichlorosilane. Silicas thus treated are known as silica dimethyl silylate according to the CTFA (8th edition, 2000). They are, for example, sold under the references Aerosil R972® and Aerosil R974® by the company Degussa, and Cab-O-Sil TS-610® and Cab-O-Sil TS-720® by the company Cabot.

Among the lipophilic gelling agents that may be used in the compositions according to the invention, mention may also be made of dextrin fatty acid esters, such as dextrin palmitates, in particular such as those sold under the names Rheopearl TL® or Rheopearl KL® by the company Chiba Flour.

It is also possible to use silicone polyamides of the polyorganosiloxane type, such as those described in documents U.S. Pat. Nos. 5,874,069, 5,919,441, 6,051,216 and U.S. Pat. No. 5,981,680.

These silicone polymers may belong to the following two families:
- polyorganosiloxanes comprising at least two groups capable of establishing hydrogen interactions, these two groups being located in the chain of the polymer, and/or
- polyorganosiloxanes comprising at least two groups capable of establishing hydrogen interactions, these two groups being located on grafts or branches.

Dyestuffs

The composition according to the invention may contain a colouring agent (also called dyestuff) which may be chosen from water-soluble or liposoluble dyes, pigments and pearlescent agents, and mixtures thereof.

The composition according to the invention may also comprise one or more dyestuffs chosen from water-soluble dyes and pulverulent dyestuffs, for instance pigments, pearlescent agents and glitter flakes that are well known to those skilled in the art. The dyestuffs may be present in the composition in a content ranging from 0.01% to 50% by weight, relative to the weight of the composition, preferably from 0.01% to 30% by weight.

The term "pigments" should be understood to mean white or coloured, mineral or organic particles, which are insoluble in an aqueous solution and which are intended to colour and/or opacify the resulting film.

The pigments may be present in a proportion of from 0.01% to 20% by weight, especially from 0.01% to 15% by weight, and in particular from 0.02% to 10% by weight, relative to the total weight of the cosmetic composition.

As mineral pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

They may also be pigments with a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The dyestuff may also comprise a pigment with a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D & C type, lakes based on cochineal carmine, or on barium, strontium, calcium or aluminium, or else the diketopyrrolopyrroles (DPPs) described in documents EP-A-542669, EP-A-787730, EP-A-787731 and WO-A-96/08537.

The term "pearlescent agents" should be understood to mean iridescent or non-iridescent coloured particles of any form, in particular produced by certain molluscs in their shell, or else synthesized, and which have a colour effect by optical interference.

The pearlescent agents may be chosen from pearlescent pigments such as titanium mica coated with an iron oxide, titanium mica coated with bismuth oxychlorides, titanium mica coated with chromium oxide, titanium mica coated with an organic dye and also pearlescent pigments based on bismuth oxychlorides. They may also be mica particles at the surface of which are superposed at least two successive layers of metal oxides and/or of organic dyestuffs.

By way of example of pearlescent agents, mention may also be made of natural mica coated with titanium oxide, with iron oxide, with natural pigment or with bismuth oxychloride.

Among the pearlescent agents available on the market, mention maybe made of the (mica-based) pearlescent agents Timica, Flamenco and Duochrome sold by the company Engelhard, the Timiron pearlescent agents sold by the company Merck, the Prestige mica-based pearlescent agents sold by the company Eckart, and the Sunshine synthetic mica-based pearlescent agents sold by the company Sun Chemical.

The pearlescent agents may more particularly have a yellow, pink, red, bronze, orangey, brown, gold and/or coppery colour or tint.

By way of illustration of the pearlescent agents that may be used in the context of the present invention, mention may in particular be made of the gold-coloured pearlescent agents sold in particular by the company Engelhard under the name Brillant Gold 212G (Timica), Gold 222C (Cloisonne), Sparkle gold (Timica), Gold 4504 (Chromalite) and Monarch gold 233X (Cloisonne); the bronze pearlescent agents sold in particular by the company Merck under the name Bronze fine (17384) (Colorona) and Bronze (17353) (Colorona) and by the company Engelhard under the name Super bronze (Cloisonne); the orange pearlescent agents sold in particular by the company Engelhard under the name Orange 363C (Cloisonne) and Orange MCR 101 (Cosmica) and by the company Merck under the name Passion orange (Colorona) and Matte orange (17449) (Microna); the brown-coloured pearlescent agents sold in particular by the company Engelhard under the name Nu-antique copper 340XB (Cloisonne) and Brown CL4509 (Chromalite); the pearlescent agents with a copper tint sold in particular by the company Engelhard under the name Copper 340A (Timica); the pearlescent agents with a red tint sold in particular by the company Merck under the name Sienna fine (17386) (Colorona); the pearlescent agents with a yellow tint sold in particular by the company Engelhard under the name Yellow (4502) (Chromalite); the red-coloured pearlescent agents with a gold tint sold in particular by the company Engelhard under the name Sunstone G012 (Gemtone); the pink pearlescent agents sold in particular by the company Engelhard under the name Tan opale G005 (Gemtone); the black pearlescent agents with a gold tint sold in particular by the company Engelhard under the name Nu antique bronze 240 AB (Timica), the blue pearlescent agents sold in particular by the company Merck under the name Matte blue (17433) (Microna), the white pearlescent agents with a silvery tint sold in particular by the company Merck under the name Xirona Silver and the golden-green pink-orange pearlescent agents sold in particular by the company Merck under the name Indian summer (Xirona), and mixtures thereof.

The term "dyes" should be understood as meaning compounds that are generally organic, which are soluble in fatty substances such as oils or in an aqueous-alcoholic phase.

The composition according to the invention may also comprise water-soluble or liposoluble dyes. The liposoluble dyes are, for example, Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

The composition according to the invention may also contain at least one material with a specific optical effect.

This effect is different from a simple conventional hue effect, i.e. a unified and stabilized effect as produced by standard dyestuffs, for instance monochromatic pigments. For the purpose of the invention, the term "stabilized" means lacking an effect of variability of the colour as a function of the angle of observation or alternatively in response to a temperature change.

For example, this material may be chosen from particles with a metallic tint, goniochromatic colouring agents, diffracting pigments, thermochromic agents, optical brighteners, and also fibres, especially interference fibres. Needless to say, these various materials may be combined so as to simultaneously afford two effects, or even a novel effect in accordance with the invention.

The particles with a metallic tint that may be used in the invention are chosen in particular from:
 particles of at least one metal and/or of at least one metal derivative,
 particles comprising a mono-material or multi-material organic or mineral substrate, at least partially coated with at least one coat with a metallic tint comprising at least one metal and/or at least one metal derivative, and mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulphides.

As illustrations of these particles, mention may be made of aluminium particles, such as those sold under the names Starbrite 1200 EAC® by the company Siberline, and Metalure® by the company Eckart.

Mention may also be made of copper metal powders or alloy mixtures such as the reference 2844 sold by the company Radium Bronze, metallic pigments such as aluminium or bronze, such as those sold under the name Rotosafe® 700 from the company Eckart, the silica-coated aluminium particles sold under the name Visionaire Bright Silver® from the company Eckart and metal alloy particles, for instance the silica-coated bronze (alloy of copper and zinc) powders sold under the name Visionaire Bright Natural Gold® from the company Eckart.

They may also be particles comprising a glass substrate, such as those sold by the company Nippon Sheet Glass under the name Microglass Metashine®.

The goniochromatic colouring agent may be chosen, for example, from multilayer interference structures and liquid-crystal colouring agents.

Examples of symmetrical multilayer interference structures that may be used in the compositions prepared in accordance with the invention are, for example, the following structures: $Al/SiO_2/Al/SiO_2/Al$, pigments having this structure being sold by the company Dupont de Nemours; $Cr/MgF_2/Al/MgF_2/Cr$, pigments having this structure being sold under the name Chromaflair by the company Flex; $MoS_2/SiO_2/Al/SiO_2MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by the company BASF; $MoS_2/SiO_2/mica$-$oxide/SiO_2/MoS_2$; $Fe_2O_3/SiO_2/mica$-$oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona® by the company Merck (Darmstadt). By way of example, these pigments may be the pigments of silica/titanium oxide/tin oxide structure sold under the name Xirona Magic® by the company Merck, the pigments of silica/brown iron oxide structure sold under the name Xirona Indian Summer® by the company Merck and the pigments of silica/titanium oxide/mica/tin oxide structure sold under the name Xirona Caribbean Blue® by the company Merck. Mention may also be made of the Infinite Colors® pigments from the company Shiseido. Depending on the thickness and the nature of the various layers, different effects are obtained. Thus, with the $Fe_2O_3/SiO_2/Al/SiO_2/Fe_2O_3$ structure, the colour changes from green-golden to red-grey for $SiO_2$ layers of 320 to 350 nm; from red to golden for $SiO_2$ layers of 380 to 400 nm; from violet to green for $SiO_2$ layers of 410 to 420 nm; from copper to red for $SiO_2$ layers of 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chemx and also the products sold under the name Helicone® HC by the company Wacker.

Additional Cosmetic Ingredients

The composition according to the invention may also comprise further cosmetic ingredients, which may be chosen for example from film-forming polymers, antioxidants, fragrances, preservatives, neutralizing agents, surfactants, sunscreens, vitamins, moisturizers, self-tanning compounds, anti-wrinkle active agents, emollients, hydrophilic or lipophilic active agents, free-radical scavengers, deodorants, sequestering agents, film-forming agents and semi-crystalline polymers, and mixtures thereof.

Of course, those skilled in the art will take care to select the optional additional ingredients and/or the amount thereof such that the advantageous properties of the composition according to the invention are not, or are not substantially, adversely affected by the envisaged addition.

Protocol for Measuring Hardness:

The measurement is carried out according to the following protocol:

The lipstick stick is stored at 20° C. for 24 hours before measuring the hardness.

The hardness can be measured at 20° C. by the "cheesewire" method, which comprises transversely cutting a stick of product, preferably a cylindrical stick generated by rotation, using a stiff tungsten wire with a diameter of 250 μm, the wire being moved relative to the stick at a rate of 100 mm/min.

The hardness of the samples of compositions of the invention, expressed in $Nm^{-1}$, is measured using a DFGS2 force gauge sold by the company Indelco-Chatillon.

The measurement is repeated three times and then averaged. The mean of the three values read using the force gauge mentioned above, denoted Y, is given in grams. This mean is converted to Newtons and then divided by L, which represents the greatest dimension traversed by the wire. In the case of a cylindrical stick, L is equal to the diameter (in metres).

The hardness is converted into $Nm^{-1}$ by the equation below:

$$(Y \times 10^{-3} \times 9.8)/L$$

For a measurement at a different temperature, the stick is stored at this new temperature for 24 hours before the measurement.

According to this method, the hardness at 20° C. of examples with a composition according to one aspect of the invention is greater than 30 $Nm^{-1}$, in particular greater than 40 $Nm^{-1}$, preferably greater than 50 $Nm^{-1}$.

According to this method, the hardness at 20° C. of examples with a composition according to one aspect of the invention is less than 500 $Nm^{-1}$, in particular less than 400 $Nm^{-1}$, preferably less than 300 $Nm^{-1}$.

In particular, the term "solid composition" is intended to mean a composition having a hardness of greater than 30 $Nm^{-1}$, preferably greater than 50 $Nm^{-1}$.

Preferably, the composition according to the invention is solid.

The term "solid" characterizes the state of the composition at ambient temperature (20° C.) and at atmospheric pressure (760 mmHg).

Advantageously, the composition according to the invention is in the form of a solid foundation, a lipstick wand or paste, a concealer product, an eye contour product, an eyeliner, a mascara, an eye shadow, a body makeup product or a skin colouring product.

In particular, the composition of the invention may be in the form of a coloured lip makeup product, such as a lipstick, a lip gloss or a lip pencil, possibly having care or treating properties.

Preferably, the composition according to the invention comprises less than 3%, or better still less than 1% of water by weight, relative to the total weight of the composition. More preferably, the composition is completely anhydrous. The term "anhydrous" is intended to mean that the water is preferably not intentionally added to the composition, but may be present in trace amounts in the various compounds used in the composition.

According to one preferred embodiment, the composition according to the invention is in the form of an anhydrous stick.

The invention is illustrated in greater detail in the following examples given by way of illustration and without being limiting in nature. The percentages are percentages by weight.

Examples 1 and 2

Lipstick in Stick Form

A lipstick composition 1 according to the invention and a comparative composition 2 not part of the invention, containing no tackifying resin, which comprises the following ingredients (amounts as percentage by weight) were prepared:

| | Starting materials (US INCI name) | Composition 1 according to the invention | Comparative composition 2 (not part of the invention) |
|---|---|---|---|
| Phase A | Octyldodecyl neopentanoate | 13.00 | 14.24 |
| | Hydrogenated poly-isobutene (Parleam from NOF Corporation) | 6.00 | 6.83 |
| | Vinylpyrrolidone/hexa-decene copolymer (Antaron V216 from ISP) | 9.00 | 9.89 |
| Phase B | Isohexadecane | 20.00 | 21.96 |
| | Hydrogenated styrene/methylstyrene/indene copolymer (Regalite R1100 from Eastman Chemical) | 8.00 | — |
| Phase C | Vinylpyrrolidone/eicosene copolymer (Antaron V220F from ISP) | 2.00 | 1.98 |
| | Polyethylene wax (Performalene 500-L from New Phase Technologies) | 11.00 | 11.97 |
| Phase D | Iron oxides | 3.43 | 3.39 |
| | Blue dye | 1.05 | 1.04 |
| | Titanium dioxide | 1.43 | 1.41 |
| | Red dye | 2.08 | 2.06 |
| Phase E | Trimethylsiloxyphenyl dimethicone (Belsil 1000 from Wacker) | 23 | 25.23 |
| | Total: | 100 | 100 |

Compositions 1 and 2 are obtained according to the following protocol:

Firstly, the fillers and the pigments of phase D are ground in a part of the oily phase A.

The rest of the liposoluble ingredients are then mixed at a temperature of about 100° C. The ground material is then added to the oily phase.

Finally, the composition is poured into a mould for obtaining sticks with a diameter of 12.7 mm, and the whole is left to cool in a freezer for approximately one hour.

The hardness of composition 1 is 104 $Nm^{-1}$ and the hardness of comparative composition 2 is 103 $Nm^{-1}$. The two compositions therefore have a similar hardness.

Two hours after application of each composition to the lips, it was observed that the deposit on the lips made with composition 1 is glossier and more comfortable (no tautness or drying out of the lips) than that made with comparative composition 2.

Thus, the presence of the Regalite R 1100 resin makes it possible to improve the staying power of the gloss and the comfort of the makeup product.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising at least one fatty phase, the at least one fatty phase comprising:
   at least one indene hydrocarbon-based resin having a number-average molecular weight of less than or equal to 10 000 g/mol,
   at least one volatile oil, and
   at least one phenyl silicone oil of formula (IV):

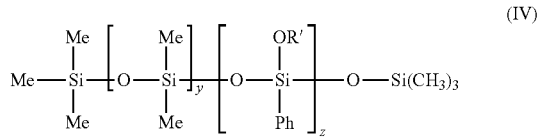

wherein
Me is a methyl group,
Ph is a phenyl group,
OR' is an —OSiMe$_3$ group,
y is 1-1000, and z is 1-1000; and
wherein a weight ratio of the phenyl silicone oil to the indene hydrocarbon-based resin is from 1/1 to 5/1.

2. The composition according to claim 1, wherein the indene hydrocarbon-based resin is obtained by polymerization of an indene monomer and of at least one monomer selected from the group consisting of styrene, methylindene and methylstyrene.

3. The composition according to claim 1, wherein the indene hydrocarbon-based resin is hydrogenated.

4. The composition according to claim 1, wherein the indene hydrocarbon-based resin is selected from the group consisting of hydrogenated copolymers of indene, methyl styrene and styrene.

5. The composition according to claim 1, wherein a content of the indene hydrocarbon-based resin is from 0.1% to 30% by weight, relative to the total weight of the composition.

6. The composition according to claim 1, wherein a content of the phenyl silicone oil is from 0.5% to 85% by weight relative to the total weight of the composition.

7. The composition according to claim 1, wherein the at least one volatile oil is a hydrocarbon-based oil selected from the group of hydrocarbon-based oils comprising from 8 to 16 carbon atoms.

8. The composition according to claim 1, wherein a content of the volatile oil is from 5% to 50% by weight relative to the total weight of the composition.

9. The composition according to claim 1, further comprising at least one additional hydrocarbon-based oil which is non-volatile.

10. The composition according to claim 9, wherein the additional non-volatile hydrocarbon-based oil is is a copolymer of vinylpyrrolidone and 1-hexadecene.

11. The composition according to claim 10, wherein a content of the additional non-volatile oil is from 0.1% to 60% by weight relative to the total weight of said composition.

12. The composition according to claim 1, further comprising a wax in a content of 0.1% to 30% by weight relative to the total weight of the composition.

13. The composition according to claim 1, wherein the composition does not comprise a wax.

14. The composition according to claim 1, further comprising at least one material selected from the group consisting of a filler, a pasty fatty substance and a dyestuff.

15. The composition according to claim 1, wherein a content of water is less than 3% by weight relative to the total weight of the composition.

16. The composition according to claim 1, wherein the composition is in solid form.

17. A method for caring for at least one of the skin and the lips, comprising applying the composition of claim 1 to the skin, to the lips or both.

18. A method for making up at least one of the skin and the lips, comprising applying the composition of claim 1 to the skin, to the lips or both.

19. The method according to claim 18, wherein the composition is applied to the lips.

* * * * *